United States Patent [19]

Joncour

[11] Patent Number: 4,650,300

[45] Date of Patent: Mar. 17, 1987

[54] LUMINOUS SOURCE FOR MEASURING DEVICE OF THE OCULAR PARAMETERS OF A SUBJECT

[75] Inventor: Christian Joncour, Villeneuve St. Georges, France

[73] Assignee: Essilor International (Compagnie Generale d'Optique), Creteil, France

[21] Appl. No.: 880,632

[22] Filed: Jun. 27, 1986

Related U.S. Application Data

[63] Continuation of Ser. No. 632,479, Jul. 19, 1984, abandoned.

[30] Foreign Application Priority Data

Aug. 5, 1983 [FR] France ................................ 83 12970

[51] Int. Cl.⁴ ............................ A61B 3/10; A61B 3/14
[52] U.S. Cl. .................................... 351/204; 351/212; 351/221
[58] Field of Search ............... 351/204, 205, 206, 207, 351/208, 211, 212, 221, 243, 247; 33/200

[56] References Cited

U.S. PATENT DOCUMENTS

| | | | |
|---|---|---|---|
| 4,046,463 | 9/1977 | La Russa et al. | 351/212 |
| 4,196,980 | 4/1980 | Heine | 351/212 |
| 4,252,420 | 2/1981 | Kohayakawa | 351/208 |

FOREIGN PATENT DOCUMENTS 964567  7/1964  United Kingdom ................ 351/221

*Primary Examiner*—Rodney B. Bovernick
*Attorney, Agent, or Firm*—Burgess, Ryan & Wayne

[57] ABSTRACT

Luminous source of device for measuring, by means of corneal reflections, the ocular parameters of a subject.

The source comprises a first extended emitting zone globally annular adapted to produce on the cornea of each eye of the subject a reflection observable by the operator of the device and a second punctual emitting zone disposed at the centre of the first emitting zone and constituting the fixation point of the subject's stare.

7 Claims, 2 Drawing Figures

LUMINOUS SOURCE FOR MEASURING DEVICE OF THE OCULAR PARAMETERS OF A SUBJECT

This application is a continuation of application Ser. No. 632,479, filed July 19, 1984, now abandoned.

BACKGROUND OF THE INVENTION

1. Field of the Invention

The present invention concerns in a general manner a device for measuring the ocular parameters of a subject especially the pupillary deviation, and concerns more particularly, a device in which this measurement is made by determining for each eye the position of the reflection on the cornea of a luminous source focused at infinity.

In a more precise manner, the present invention concerns a luminous source for such a device, which source is intended to produce a reflection on the cornea of each eye.

2. Description of the Prior Art

In known devices, such as that described in French Patent published under No. 1.506.352, the luminous source that is used is constituted by a filament lamp. This source which is placed at the focus of a lens constitutes first a fixation point, projected to infinity by the lens, for the subject whose ocular parameters it is desired to measure. The second essential function of this luminous source is to form on the cornea of each of the subject's eyes a reflection that can be observed by the operator of the device.

The operator who observes the subject's eyes and consequently observes each corneal reflection can superimpose on each of them a horizontally movable vertical reticle so as to determine the pupillary distance between the centers of the subjects pupils and a vertically movable horizontal reticle to determine the distance separating the centre of each pupil from the lower part of a spectacle frame worn by the subject.

The luminous source must have a range sufficient to be able to produce on the cornea of each eye a reflection, observable by the operator but it must also be small enough to completely fix at infinity the subject's stare. These two antinomic conditions lead to using a luminous source having a size such that it impairs the measuring precision of the device, taking into account especially the difficulty for the operator of centering a reticle on a reflection of a dimension clearly greater than the width or the thickness of the reticle.

The present invention overcomes this major drawback by proposing a luminous source for fulfilling the two conditions set out above.

The luminous source according to the invention is essentially characterized in that it comprises a first extended substantially perimetric emitting zone, adapted to produce on the cornea of each eye of the subject a reflection that can be observed by the operator and a second point emitting zone disposed at the centre of the first zone and constituting the fixation point of the subject's stare.

Accordingly, the subject can fix his sight on the second point emitting zone, this second zone being small enough not to produce any corneal reflection observable by the operator.

The first perimetric extended emitting zone will produce for itself a corneal reflection with perfectly defined outlines, and a dark central part, allowing the operator an easy and rapid centering of the reticles on the said corneal reflection.

According to a first embodiment of the invention the wavelengths of the first and second emitting zones are different and preferably have a value respectively comprised between 6.500 and 8.000 angströms and between 5.000 and 6.000 angströms.

According to another preferred embodiment, the first perimetric emitting zone, is constituted by four electroluminescent diode strips, each of them being centered on one side of a square.

In an equally advantageous manner, the second emitting zone is constituted by a point electroluminescent diode.

BRIEF DESCRIPTION OF THE DRAWINGS

The characteristics and advantages of the invention will appear from the following description given with reference to the appended drawings in which.

DETAILED DESCRIPTION OF THE INVENTION

Figure 1:
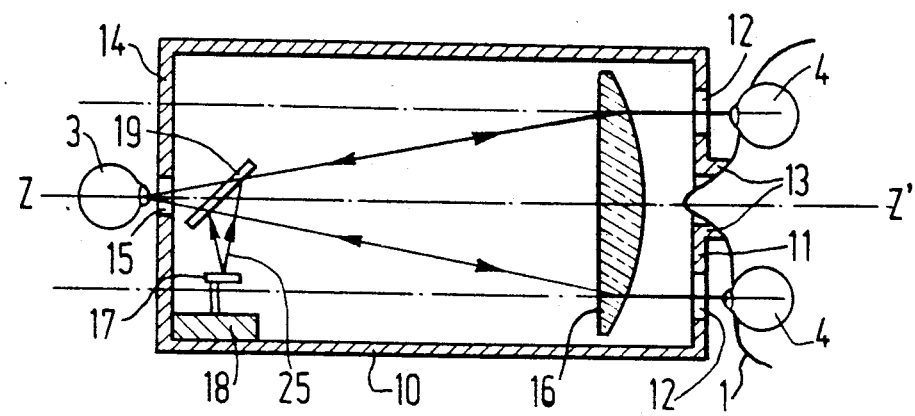
FIG. 1 is a general diagram in section of a known device for measuring the ocular parameters of a subject.

According to FIG. 1, the device for measuring ocular parameters of a subject schematically indicated at 1 comprises a housing 10, with a front wall 11 in which are provided two openings 12. On the front wall 11, between the two openings 12 are provided possibly removable and adjustable pads 13 to permit positioning the device in front of the subject 1 by resting on his nose.

In the rear wall portion 14 of the housing opposite the front wall 11 is provided an opening 15 allowing the operator schematically shown at 3 to observe the eyes 4 of the subject through the openings 12.

Inside the housing 10 is placed a lens 16 at the reflective focus of which is disposed a luminous source 17 connected to a feed source 18.

In order to allow the operator to observe without interference the eyes 4 of the subject 1, the source 17 is shifted by 90° with respect to the axis ZZ' of the lens 16, a semi-reflecting mirror 19 being interposed in the path of the luminous beam 25 issuing from the source 17 to direct it towards the eyes 4.

The operator by one of his eyes 3 that he sets on the axis ZZ' substantially at the focus of the lens 16 observes the reflections of the source 17 on the corneas of the eyes 4.

Figure 2:
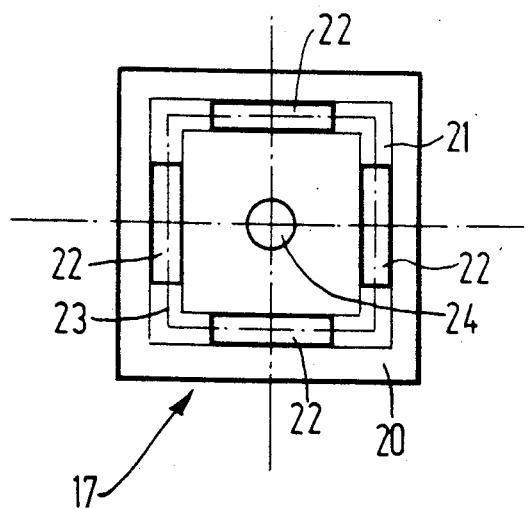
FIG. 2 is a view from above showing the structure of an embodiment of a luminous source according to the invention, to be used in the device of FIG. 1.

The source 17 represented in FIG. 2 comprises a support 20, for example, having a square shape.

The source 17 comprises a first perimetric emitting zone schematically indicated by the ring 21 which is represented by thin lines.

With the aim of enhanced simplicity, the embodiment of this first perimetric emitting zone, four electroluminescent diode strips 22 are fixed on the support 20 and centered on each side of a square 23, itself centered on the perimeter 21.

The source 17 also comprises a second point emitting zone 24 disposed at the centre of the perimeter 21 and constituted by an electroluminous diode.

The wavelengths of the first emitting zone is preferably comprised between 6.500 and 8.000 angströms substantially corresponding to one of the red radiations of the visible spectrum, whereas the wavelength of the second emitting zone, different from that of the first, is comprised between 5.000 and 6.000 angströms substantially corresponding to the green-yellow zone of the visible spectrum.

The second point emitting zone constitutes for the subject the fixation point of his stare and allows to fix it perfectly, due to its small size. Furthermore, due to the limited emitting surface of the print source, the operator will not perceive any corneal reflection due to this second zone.

By observing the eyes of the patient through the opening 15, the operator will perceive on each eye 4 of the subject, a corneal reflection from the first emitting zone 21. He could thus perfectly centre on the said reflection, its geometry corresponding exactly to that of the first emitting zone, the movable reticles provided for this purpose in the windows 12 and thus determine with precision the ocular parameters of the subject.

Of course the present invention is in no way limited to the embodiment described and represented hereinabove but, on the contrary, encompasses all possible variants.

What is claimed is:

1. In a device for measuring ocular parameters of a subject based on corneal reflections observed by an operator, which device comprises lens means for transmitting light to the eyes of the subject and for focusing the light reflected by the corneas of the subject's eyes onto a viewing location at which at least one of the operator's eyes is enabled to observe said reflections, and a semi-reflecting mirror placed on the optical axis of said lens means, said mirror being inclined with respect to said axis and located between said lens means and the direct focus thereof so as to define in addition to said direct focus a reflected focus angularly shifted with respect to said direct focus, the improvement which comprises:

a light source for producing said light to be directed to the subject's eyes through the intermediary of said semi-reflecting mirror, said light source comprising a substantially perimetric light emitting zone and a substantial point light emitting zone located at the center of the area surrounded by said perimetric zone, said point emitting zone being located at one of said focuses, said viewing location is placed at the other one of said focuses, whereby the light emitted by said perimetric emitting zone produces said corneal reflections adapted to be observed from said viewing location, while the light emitted by said point emitting zone defines a point for fixing the subject's stare during the observation of said corneal reflections, said perimetric emitting zone being radially spaced from said point emitting zone.

2. The light source claimed in claim 1, wherein said perimetric emitting zone comprises four electroluminescent diode strips disposed along the four sides of a square, respectively.

3. The light source claimed in claim 1, wherein said point emitting source comprises an electroluminous diode component.

4. The light source claimed in claim 1, wherein the light emitted by said perimetric emitting zone has a wavelength different from that of the light emitted by said point emitting zone.

5. The light source claimed in claim 4, wherein the light emitted by said perimetric emitting zone has a wavelength comprised between 6500 and 8000 angstroms.

6. The light source claimed in claim 4, wherein the light emitted by said point emitting zone has a wavelength comprised between 5000 and 6000 angstroms.

7. The light source claimed in claim 1, wherein said point light emitting zone is located at said reflected focus, while said viewing location is defined by said direct focus.

* * * * *